(12) United States Patent
Van Zijl et al.

(10) Patent No.: US 7,683,617 B2
(45) Date of Patent: Mar. 23, 2010

(54) NON-INVASIVE MRI MEASUREMENT OF TISSUE GLYCOGEN

(75) Inventors: Peter C. M. Van Zijl, Ellicott City, MD (US); Craig K. Jones, Ilderton (CA)

(73) Assignees: Johns Hopkins University, Baltimore, MD (US); Kennedy Krieger Institute, Baltimore, MD (US)

(*) Notice: Subject to any disclaimer, the term of this patent is extended or adjusted under 35 U.S.C. 154(b) by 36 days.

(21) Appl. No.: 11/996,162

(22) PCT Filed: Jul. 21, 2006

(86) PCT No.: PCT/US2006/028314

§ 371 (c)(1),
(2), (4) Date: Jan. 18, 2008

(87) PCT Pub. No.: WO2007/014004

PCT Pub. Date: Feb. 1, 2007

(65) Prior Publication Data

US 2008/0197840 A1    Aug. 21, 2008

(51) Int. Cl.
*G01V 3/00* (2006.01)

(52) U.S. Cl. .................. 324/309; 324/307
(58) Field of Classification Search ......... 324/300–322; 600/407–445
See application file for complete search history.

(56) References Cited

U.S. PATENT DOCUMENTS

| | | | | |
|---|---|---|---|---|
| 5,475,308 A | * | 12/1995 | Piotto et al. | 324/307 |
| 7,253,620 B1 | * | 8/2007 | Derbyshire et al. | 324/307 |
| 2008/0167549 A1 | * | 7/2008 | Balaban et al. | 600/420 |

* cited by examiner

*Primary Examiner*—Brij B Shrivastav
(74) *Attorney, Agent, or Firm*—Fay Sharpe LLP

(57) ABSTRACT

In a method for deriving information about a selected monosaccharide or polysaccharide such as glucose or glycogen, a selected modification such as saturation is made of magnetic resonance at a magnetic resonance frequency of protons of hydroxyl groups of the selected monosaccharide or polysaccharide. Probative water proton magnetic resonance data are acquired while the selected modification is substantially in effect. Information is derived about concentration or density of the selected monosaccharide or polysaccharide based at least on the probative water proton magnetic resonance data.

24 Claims, 9 Drawing Sheets

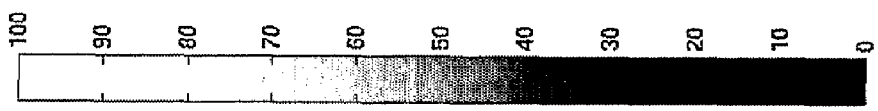
Fig. 9

NON-INVASIVE MRI MEASUREMENT OF TISSUE GLYCOGEN

DESCRIPTION

The following relates to the biological and medical arts. It is described with example reference to in vivo spatially resolved detection, imaging, or mapping of glycogen in human tissue. However, the following relates more generally to spatially resolved detection, imaging, or mapping of endogenous glycogen or glucose in various types of plant, animal, human, or other biological tissue or samples.

Glucose is a monosaccharide, or simple sugar. Glycogen is a polysaccharide made up of glucose building blocks. Glycogen is a principal form of energy storage in the human body. Typically, glucose is eaten in pure form or generated during digestion and may be present in substantial quantities in the stomach. After uptake and transport in blood, it can be transferred into tissue, where it serves as direct source for metabolism or is integrated into polysaccharides such as glycogen for storage. Stored glycogen can be metabolized to release energy for use in biological processes in the human body. For example, the liver contains a substantial store of glycogen that can be converted to glucose, which can then be metabolized. Glycogen is also present in substantial quantities in muscle tissue, where it provides a ready reserve of energy for muscular activity.

There are various diseases or disorders that are or may be related to problems in glycogen production, storage, or metabolism. These include, for example: diabetes; malnutrition; weight disorders; various metabolic disorders; at least eight different glycogen storage diseases; phosphofructokinase deficiencies; cardiac disease; ischemia; myocardial viability; muscular dystrophies; congenital myopathies; cancer; alcoholism; hepatitis; and liver disease. Spatially resolved detection, imaging, or mapping of glycogen is of value in detecting, diagnosing, and monitoring such diseases and disorders. Wellness and sports medicine can also benefit from spatially resolved detection, imaging, or mapping of glycogen. For example, sports medicine can utilize such diagnostics to understand and optimize usage of glycogen during exercise, while dietary medicine can use such diagnostics to monitor digestion and usage of various foods. An existing technique for spatially resolved detection of glycogen is magnetic resonance spectroscopy (MRS) of the $^{13}C$ label in glycogen. This can be done both with direct $^{13}C$ detection or proton-detected $^{13}C$ MRS. For recent reviews: Shulman R G, Rothman D L. NMR of intermediary metabolism: implications for systemic physiology. Annu Rev Physiol. 2001;63: 15-48. Price T B, Rothman D L, Shulman R G. NMR of glycogen in exercise. Proc Nutr Soc. 1999 November:58(4): 851-9; Shulman R G, Rothman D L, Price T B. Nuclear magnetic resonance studies of muscle and applications to exercise and diabetes. Diabetes. 1996 January:45 Suppl 1:S93-8. Roden M, Petersen K F, Shulman G I, Nuclear Magnetic Resonance Studies of Hepatic Glucose Metabolism in Humans. Recent Progress in Hormone Research. 2001, 56, 219-237. There are two types of approaches. In the first, the natural abundance level of $^{13}C$ is used to measure glycogen content or glycogen metabolism or both. In the second approach, a subject receives a $^{13}C$-labeled substrate (e.g. $^{13}C$-glucose or other compounds) by ingestion, intravenously, or so forth, after which the $^{13}C$ atoms are incorporated into glycogen. Magnetic resonance spectroscopy or spectroscopic imaging (MRSI) is then tuned to detect the $^{13}C$-related magnetic resonance signal. These approaches have disadvantages, however. For both approaches, the low concentration of $^{13}C$ atoms generally leads to coarse spatical resolution and a weak magnetic resonance signal. Also, the equipment and pulse sequences to perform $^{13}C$-MR or proton-detected $^{13}C$ MR are not standard on most clinical scanners. For the second approach, the requirement of administration of the $^{13}C$-labeled substrate is often problematic.

The present application provides new and improved apparatuses and methods for spatially resolved detection, imaging, or mapping of endogenous glycogen or glucose in tissue in situ, which overcome the above-referenced problems and others.

Apparatus and method embodiments are disclosed.

In an example magnetic resonance method, a magnetic labeling, such as saturation or non-invasive magnetic labeling, is made at a magnetic resonance frequency of exchangeable protons of hydroxyl (—OH) groups of a selected endogenous monosaccharide or polysaccharide. Probative water proton magnetic resonance data are acquired after the magnetic labeling has been applied and while the influence of this modification on water is substantially in effect. Information about concentration or density of the selected monosaccharide or polysaccharide is derived based at least on the probative water proton magnetic resonance data.

In an example apparatus embodiment, means are provided for making a selected in vivo modification, such as saturation or labeling, at a magnetic resonance frequency of protons of hydroxyl groups of a selected endogenous monosaccharide or polysaccharide. Means are provided for acquiring in vivo probative water proton magnetic resonance data after the magnetic labeling has been applied and while the influence of this modification on water is substantially in effect. Means are provided for deriving information about in vivo concentration or density of the selected monosaccharide or polysaccharide based at least on the probative water proton magnetic resonance data.

In an example magnetic resonance apparatus, a magnetic resonance scanner includes a main magnet generating a main magnetic field in an examination region, a magnetic field gradient system for superimposing selected magnetic field gradients on the main magnetic field in the examination region, and a radio frequency system for exciting and acquiring magnetic resonance in the examination region. A controller is configured to cause the magnetic resonance scanner to (i) saturate at a glycogen hydroxyl proton magnetic resonance frequency while substantially not saturating at the water proton magnetic resonance frequency and (ii) acquire magnetic resonance at the water proton magnetic resonance frequency. A data processor is configured to derive information about endogenous glycogen or glucose in tissue based on the acquired magnetic resonance at the water proton magnetic resonance frequency.

One advantage resides in providing in vivo spatially resolved detection, imaging, or mapping of endogenous glycogen or glucose concentrations or density.

Another advantage resides in providing in vivo spatially resolved detection, imaging, or mapping of endogenous glycogen or glucose concentrations or density without the use of an administered contrast agent.

Another advantage resides in providing in vivo spatially resolved detection, imaging, or mapping of endogenous glycogen or glucose concentrations or density using the water proton magnetic resonance signal which has typically high signal strength and signal-to-noise ratio.

Another advantage resides in providing in vivo spatially resolved detection, imaging, or mapping of endogenous glycogen or glucose concentrations or density at standard clinical scanners without need for additional hardware.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a magnetic resonance imaging system configured to perform spatially resolved detection, imaging, or mapping of glycogen or glucose.

FIG. 2 shows so-called z-spectra (see R. G. Bryant, Annu. Rev. Biophys. Biomol. Struct. vol. 25, pp. 29-53 (1996)) or CEST-spectra (see K. M. Ward, A. H. Aletras, R. S. Balaban, J. Magn. Reson. vol. 143, pp. 79-87 (2000)) for 1 mM glycogen in buffer solution and in a mixture with agarose (2%). The ordinate is $S/S_0$ which gives the signal of water protons (S) during irradiation at the frequency indicated on the abscissa, compared to that without irradiation ($S_0$).

FIG. 3 shows magnetic resonance images at 3 Tesla of a 4% glycogen phantom at physiological pH as a function of frequency offset (Hz) of the saturation radio frequency pulse. Saturation frequency in Hz is noted above and to the left of each phantom image.

FIG. 4 plots relative signal intensity ($S(\omega)/S_0 100$) for the 0%, 2%, and 4% glycogen phantoms.

FIG. 5 shows axial image slices acquired between thoracic vertebrae T8 and T9 of a human volunteer subject in a 3 Tesla magnet after saturation at a resonance frequency $\omega$. The saturation frequency $\omega$ respective to the water line (0.0 Hz) is labeled at the upper left of each image.

FIG. 6 shows an axial reference image acquired between thoracic vertebrae T8 and T9 of a human volunteer subject. Data were acquired at 3 Tesla and the human had fasted for about 18 hours. A region of interest (102) is indicated.

FIG. 9 shows an image or map of the integral under the asymmetry curve for each voxel in the images of FIG. 6 for the condition of before eating after 18 hours of fasting (left side image) and for the condition of thirty minutes after eating (right hand image).

Figure 1:
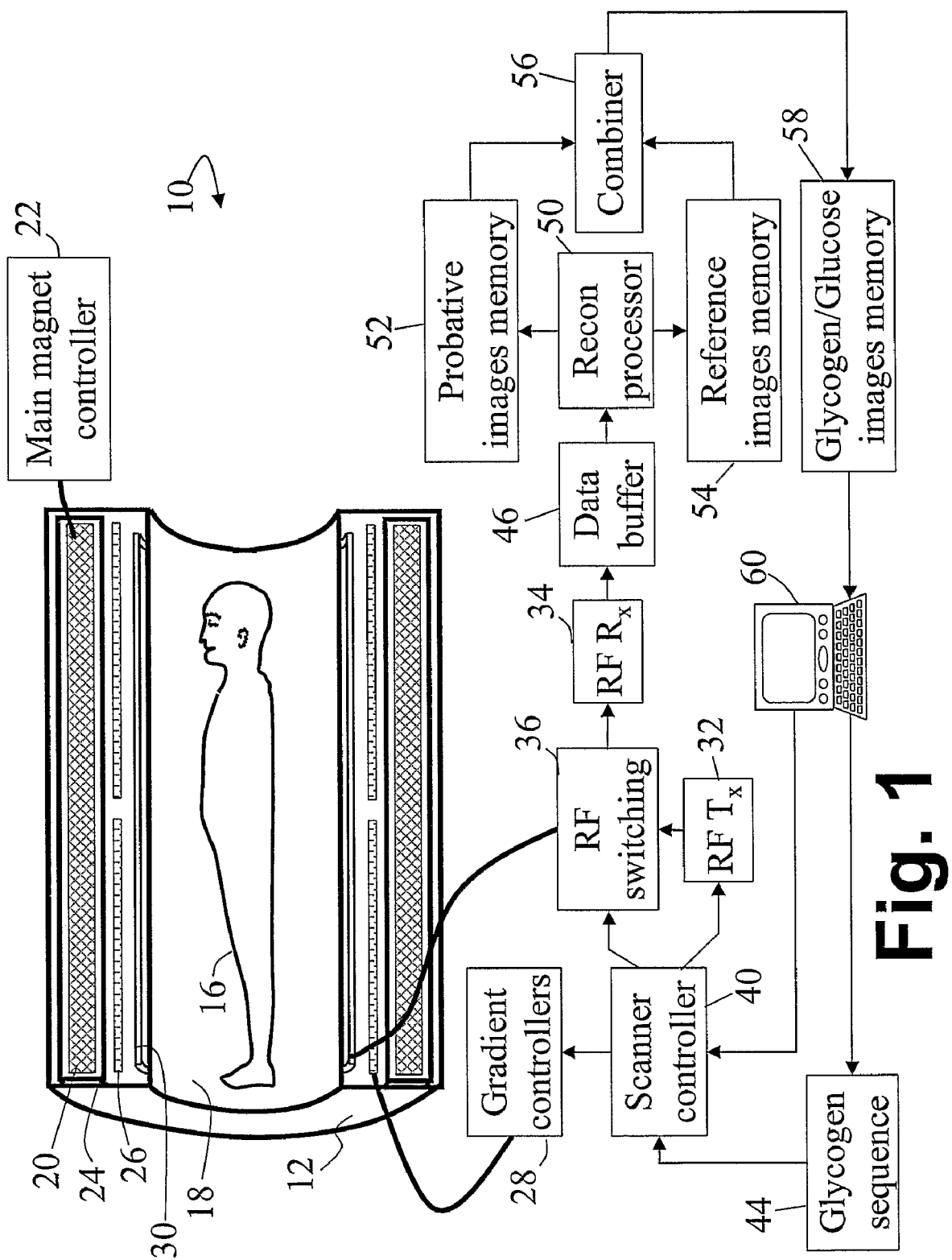

The approaches disclosed herein for spatially resolved detection, imaging, or mapping of endogenous glycogen or glucose using magnetic resonance imaging of the water signal leverage several advantageous aspects of the human body and other typical biological systems containing glycogen or glucose. On such aspect is that the human body is principally made up of water. Accordingly, magnetic resonance data acquisition at the water proton magnetic resonance frequency typically results in a large signal and signal-to-noise ratio. (In contrast, current spectroscopy and spectroscopic imaging approaches for example based on the $^{13}C$ magnetic resonance typically results in a substantially lower signal and lower signal-to-noise ratio).

Another aspect is a linkage of the population or pool of endogenous glucose or glycogen molecules and the population or pool of water molecules at typical body pH levels (e.g., pH~7.0-7.3) as well as at other pH values such as those that may occur during ischemia (pH ~5.5-7.0). These populations are linked by exchange of protons between the water molecules and protons of the hydroxyl (OH) groups of endogenous glucose or glycogen. Similar types of proton exchange have previously been observed for urea (Guivel-Scharen et al., Detection of Proton Chemical Exchange between Metabolites and Water in Biological Tissues, J. Magn. Reson. vol. 133, pages 36-45 (1998)) and for amide protons (Van Zijl et al., U.S. Pat. application Ser. No. 2004/0030239 A1 published Feb. 12, 2004). Contrary to results by Guivel-Scharen et al. in liver and heart (muscel), who found no in situ saturation transfer effects on the water signal for irradiation at frequency differences of less than ±2 ppm (in heart) and ±3 ppm (in liver) with the water resonance, inventors have found that a strong proton exchange effect exists for endogenous glycogen and glucose in frequency range of about 0.5-2.0 ppm (FIG. 2), and that this exchange effect is substantial enough to provide quantitative in vivo detection, imaging, or mapping of endogenous glycogen or glucose in the human body. The method used by Guivel-Scharen was sensitive to changes at 1 ppm, as proven by the kidney data, where such effects were detected. Notice that the results of Guivel-Scharen et al. showing no effect around 1 ppm in liver and heart therefore implicate absence of a glycogen effect, which would lead those skilled in the art to conclude that glycogen detection in tissue is not possible using the chemical exchange approach. Each glucose molecule includes five hydroxyl groups; accordingly, if a glycogen molecule is made up of N glucose building blocks, then the glycogen molecule basically contains about 43×N hydroxyl groups, as two ends per glucose unit are connected. Since a typical glycogen molecule may include hundreds, thousands, or tens of thousands of glucose building blocks, the number of hydroxyl protons available for exchange with protons of the surrounding water molecules is substantial, even if not all are water accessible.

Yet another aspect is the existence of a small chemical shift difference (range maximum of about 0.5-2.0 ppm) between the magnetic resonance frequency of water protons and the magnetic resonance frequency of protons of glucose or glycogen hydroxyl groups. The approaches disclosed herein for spatially resolved detection, imaging, or mapping of glycogen or glucose take advantage of this small chemical shift difference to separately manipulate and detect resonance from magnetic resonance of glucose or glycogen hydroxyl groups protons, on the one hand, and water protons on the other hand. Consequentially, these experiments will be more readily performed at higher magnetic fields because the chemical shift difference in Hz is proportional to the magnetic field strength, although the experiments can also be performed at lower magnetic fields.

In one example approach, protons of the glycogen or glucose hydroxyl groups are saturated, and then imaging is performed at the water proton magnetic resonance frequency. Because the imaging uses the predominant water proton species, a strong magnetic resonance signal is achieved. However, because of proton exchange between water and hydroxyl groups of glucose and glycogen, this strong water proton magnetic resonance signal is suppressed somewhat by transfer of saturated protons from the glycogen or glucose hydroxyl groups to water molecules. The extent of signal suppression is related to a dynamic equilibrium balance of saturated protons that have transferred to water molecules at any given time. This balance is determined principally by the concentration or density of glucose or glycogen molecules, the amount of saturation that can be achieved before exchange, and the pH-dependent proton exchange rate, with secondary effects due to water concentration or density and the magnetic relaxation time T1 of water. Consequentially, these experiments will be facilitated at higher magnetic fields because the T1 increases with the magnetic field strength, although the experiments can also be performed at lower magnetic fields.

With reference to FIG. 1, an example magnetic resonance apparatus suitable for spatially resolved detection, imaging, or mapping of glycogen or glucose is described. A magnetic resonance scanner 10 includes a scanner housing 12 in which a patient 16 or other subject is at least partially disposed. A protective insulating bore liner 18 optionally lines a generally cylindrical bore or opening of the scanner housing 12 inside of which the subject 16 is disposed. A main magnet 20 disposed in the scanner housing 12 is controlled by a main magnet controller 22 to generate a static (B0) magnetic field in at least a scanning region including at least a portion of the subject 16. Typically, the main magnet 20 is a persistent superconducting magnet surrounded by cryoshrouding 24.

The chemical shift (as expressed in units of Hz) between tissue water protons and protons of endogenous glucose or glycogen hydroxyl groups generally increases with increasing magnetic field strength. Accordingly, it is generally advantageous to use a high $B_0$ magnetic field strength. In some embodiments, the main magnet 20 generates a main magnetic field of at least about 3 Tesla. In some embodiments the main magnet 20 generates a main magnetic field of at least about 7 Tesla. Other main ($B_0$) magnetic field strengths, including lower field strengths, can also be used, however.

A magnetic field gradient system is provided to superimpose selected magnetic field gradients on the main ($B_0$) magnetic field. In the illustrated apparatus example of FIG. 1, a magnetic field gradient system includes magnetic field gradient coils 26 and gradient controllers 28. The magnetic field gradient coils 26 are arranged in or on the housing 12 to superimpose selected magnetic field gradients on the main magnetic field in at least the scanning region. Typically, the magnetic field gradient coils 26 include coils for producing three orthogonal magnetic field gradients, such as x gradient, y gradient, and z gradient.

A radio frequency system is provided to excite and detect magnetic resonance. In the illustrated example apparatus of FIG. 1, the radio frequency system includes a generally cylindrical quadrature body coil 30, such as a birdcage coil or a transverse electromagnetic (TEM) coil, mounted substantially coaxially with the bore of the magnetic resonance scanner 10. This coil 30 is only an example—in other embodiments another type of radio frequency coil such as a surface coil, local head coil, local torso coil, array of surface coils, various combinations thereof, or so forth may be included. A given radio frequency coil may be a transmit coil, a receive coil, or a transmit/receive coil. In the illustrated example apparatus of FIG. 1, the radio frequency coil 30 is a transmit/receive coil, and the radio frequency system further includes a radio frequency transmitter 32, a radio frequency receiver 34, and suitable switching circuitry 36 for switching between transmit and receive modes.

In operation, a scanner controller 40 operates the magnetic field gradient system 26, 28 and the radio frequency system 30, 32, 34, 36 in accordance with a glycogen sequence 44 to acquire probative magnetic resonance data with saturation of protons of the glycogen or glucose hydroxyl groups, and to acquire reference magnetic resonance data without saturation of protons of the glycogen or glucose hydroxyl groups. The acquired data are stored in a data buffer 46. In some embodiments, the magnetic resonance data are imaging data that are spatially encoded using a suitable spatial encoding technique, and a reconstruction processor 50 processes the acquired probative magnetic resonance imaging data to generate probative images that are stored in a probative images memory 52, and processes the reference magnetic resonance imaging data to generate reference images that are stored in a reference images memory 54. A combiner 56 combines the probative and reference images to derive a endogenous glycogen or glucose image that is stored in a glycogen or glucose images memory 58.

In some embodiments, rather than acquiring images with and without saturation, images are instead acquired with saturation at a plurality of frequencies encompassing the water proton magnetic resonance frequency and the magnetic resonance frequency of protons of hydroxyl groups of endogenous glucose or glycogen (0.5-2.0 ppm) and frequencies opposite these with respect to the water frequency. Imaging data are acquired and reconstructed after saturating at each frequency, and the images corresponding to saturating most closely to the magnetic resonance frequency of protons of hydroxyl groups of glucose or glycogen are determined by post-acquisition or post-reconstruction analysis of these data sets.

In the illustrated embodiment, a user interface 60 is provided, which performs both interfacing with the magnetic resonance scanner 10 and image display tasks. In other embodiments, separate control and image display interfaces may be provided. Moreover, it is to be appreciated that the illustrated system of FIG. 1 including the illustrated magnetic resonance scanner 10 are illustrative examples. The techniques disclosed herein for spatially resolved detection, imaging, or mapping of endogenous glycogen or glucose can be practiced with substantially any type of magnetic resonance scanner or apparatus, including for example the illustrated horizontal bore-type scanner 10, or a vertical bore scanner, or an open bore scanner, or so forth. Moreover, while imaging applications are described, it will be appreciated that the techniques disclosed herein for spatially resolved detection, imaging, or mapping of endogenous glycogen or glucose can be practiced with or without imaging. For example, in some embodiments the magnetic field gradients are merely applied to localize the magnetic resonance data acquisition to a defined spatial region such as a single voxel, a single slice, or so forth, for example within the liver which typically contains a high concentration or density of glycogen. The resulting probative and reference magnetic resonance data provides information about glycogen or glucose in the selected region (e.g., the liver), but does not provide an image. On the other hand, if the probative and reference magnetic resonance data are acquired with suitable Cartesian, spiral, or other spatial encoding and suitable reconstruction applied, then the resulting information about glycogen or glucose is in the form of an image indicative of the distribution of glycogen or glucose in the imaged region.

Having described suitable apparatuses for performing the techniques for spatially resolved detection, imaging, or mapping of endogenous glycogen or glucose using magnetic resonance, some example techniques for deriving information about glycogen or glucose from the probative and reference magnetic resonance data or images are next described.

When the protons of hydroxyl groups of glucose or glycogen are selectively irradiated with the correct proton magnetic resonance (i.e., nuclear magnetic resonance or NMR) frequency, they are fully or partially saturated. Because of the fast chemical exchange with water protons, this saturation can be detected through acquiring data at the water frequency. In order to verify or quantify the effect on the water signal intensity due to glycogen, a reference measurement is necessary. In one suitable approach, the water saturation due to irradiation of the protons of hydroxyl groups of glycogen or glucose at 0.5-2.0 ppm are compared with irradiation applied at a reference frequency located at the opposite frequency with respect to the water resonance (−0.5 to −2.0 ppm), or otherwise away from the glycogen or glucose hydroxyl groups proton resonance. For instance, if the water resonance is taken as 0 ppm and the glycogen protons are at 1 ppm, then a suitable reference frequency would be at −1 ppm. The exchange of the hydroxyl (OH) protons in glycogen with protons of water can be detected as a difference between the normalized water signal intensities $(S(-\omega)/S_0 - S(+\omega)/S_0)$ obtained by irradiating at the two frequencies $S(+\omega)$ and $S(-\omega)$ on opposite sides of the water line, where $S_0$ is a reference signal acquired without saturation. Another way of normalizing would be $(S(-\omega)/S(-\omega) - S(+\omega)/S(-\omega))$, in which case no reference signal $S_0$ without saturation needs to be acquired.

Figure 2:
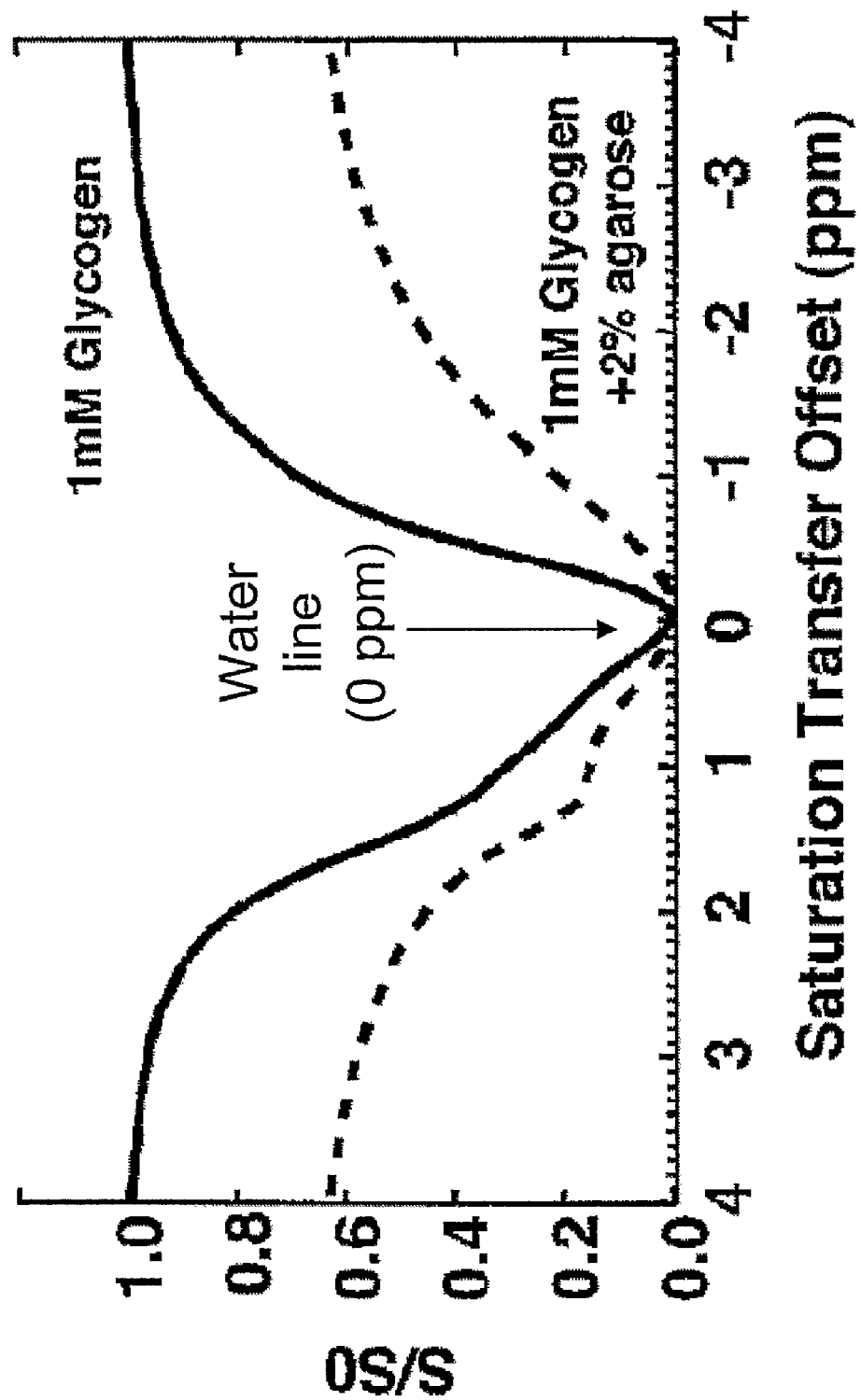

With reference to FIG. 2, in a variant approach, a series of frequencies spanning the endogenous glycogen or glucose hydroxyl proton frequency and the tissue water resonance can be irradiated and the water signal intensity can be studied as a function of saturation frequency. The plot of $S(\omega)/S_0$ where $S(\omega)$ is the signal with irradiation at frequency $\omega$ and $S_0$ is the signal without radiation is referred to as a z-spectrum. In some embodiments, a partial z-spectrum including a few such frequencies $\omega$ may be acquired instead of a full z-spectrum. FIG. 2 shows an example z-spectrum for phantom studies on proton exchange transfer on glycogen obtained at a field strength of 11.7 T, where $S/S_0$ gives the signal of water protons (S) during irradiation at the frequency indicated on the horizontal scale, compared to that without irradiation ($S_0$). FIG. 2 shows z-spectra obtained on two different phantoms containing a high molecular-weight glycogen solution (about 250-300 glucose units, where 1 mM glycogen is about 250-300 mM glucose units). The solid line is for a solution in physiological buffer. The signal is lowest at $\omega=0$ ppm since this corresponds to directly saturating the water protons. Additionally, however, the z-spectrum of FIG. 2 shows maximal asymmetry around +1 ppm due to suppression of the water proton magnetic resonance signal due to exchange with saturated protons of hydroxyl groups of the glycogen. Due to the fact that there are multiple glucose units or building blocks per glycogen molecule and multiple (typically three) hydroxyl (OH) groups per glycogen unit, the actual concentration of hydroxyl groups is very high. The exchange rate with water of protons of these hydroxyl groups under physiological conditions is substantial, being typically at about 2000-10000 Hz, or even a larger range, depending on pH. Accordingly, direct irradiation to saturate the protons of these hydroxyl groups gives an equilibrium transfer of protons that is detectable in the z-spectrum. Indeed, the proton transfer effect can be detected when the glycogen is in a semi-solid environment (agar solution in this example phantom, results plotted as a dashed line in FIG. 2). This latter semi-solid environment is similar to certain in vivo conditions of endogenous glycogen in the human body, in which the semi-solid matrix causes a large background conventional magnetization transfer effect (MT effect).

The presence of endogenous glycogen appears as an asymmetry in the z-spectrum of the water line (e.g., FIG. 2), displaying a decrease in the measured signal intensity at high frequency. This is a quantifiable effect:

$$S_{asym}(\omega) = S(-\omega)/S_0 - S(+\omega)/S_0 \qquad (1),$$

where in Equation (1) $S(+\omega)$ denotes the water signal after saturating at $+\omega$, $-\omega$ denotes the magnetic resonance frequency symmetrically positioned on the opposite side of the water proton magnetic resonance frequency from $+\omega$, and $S(-\omega)$ denotes the water signal after saturating at $-\omega$. In this case the presence of the magnetic resonance frequency of protons of hydroxyl groups of glycogen or glucose at $+\omega$ causes the asymmetry, This analytic approach is formally similar to that applied in contrast agent-mediated chemical exchange saturation transfer (CEST). See, for example: Ward et al., A New Class of Contrast Agents for MRI Based on Proton Chemical Exchange Dependent Saturation Transfer (CEST), J. Magn. Reson. vol. 143, pages 79-87 (2000); and Balaban et al., U.S. Pat. No. 6,963,769. However, in the present embodiments, Equation (1) relates to the analysis of endogenous glycogen or glucose in the human body or other in vivo biological tissue, whereas CEST relates to analysis of an exogenous contrast agent that is administered to the subject. Endogenous measurements have previously been tried by Guivel-Scharen et al., but, contrary to the data by the investigators here given negative results. Consequently, the data by Guivel-Scharen et al. deny the possibility to detect glycogen, but the current results by the inventors shows it is possible. In addition to referencing with respect to S(0), it is also possible to reference with respect to $S(-\omega)$. Because saturation depends on the power level of the radiofrequency irradiation, this latter approach will give asymmetries that are less power dependent.

The signal intensity dependence of the water signal responsive to irradiation of the exchangeable protons of glycogen or glucose can be described exactly by the Bloch equations. See, for example: Forsen et al., Study of Moderately Rapid Chemical Exchange Reactions by Means of Nuclear Magnetic Double Resonance, J. Chem. Phys. vol. 39, pages 2892-2901 (1963); Gutowsky et al., Dissociation, Chemical Exchange, and the Proton Magnetic Resonance in Some Aqueous Electrolytes, J. Chem. Phys. vol. 21, pages 1688-1694 (1953); McConnell, Reaction rates by nuclear magnetic resonance, J. Chem. Phys vol. 28, pages 430-31 (1958); and Zhou et al., Quantitative Description of Proton Exchange Processes between Water and Endogenous and Exogenous Agents for WEX, CEST, and APT Experiments, Magn Reson. Med. vol. 51, pages 945-52 (2004). To judge the effect and the parameters influencing it, a simplified analytical solution can be used (Zhou et al., Magn Reson. Med. vol. 51, pages 945-52 (2004)) when assuming that a steady state is reached instantaneously upon saturation of the saturable protons of glycogen or glucose (notice that this is not the same as complete saturation and that this approximation may not apply at higher exchange rates, where the full Bloch equations need to be used). The following expression can be derived for the proton transfer ratio (PTR):

$$PTR = \frac{S_0 - S(\omega)}{S_0} = \frac{k_{exch} \cdot \alpha \cdot x_{glyc}}{R_{1w} + k_{exch} \cdot x_{glyc}} \cdot \left[1 - e^{-(R_{1w} + k_{exch} \cdot x_{glyc}) t_{sat}}\right], \qquad (2)$$

where, in Equation (2), $k_{exch}$ is the forward glycogen- or glucose-to-water single-proton exchange rate, $R_{1w}$ the longitudinal exchange rate of water that is equal to 1/T1 for water, $x_{glyc}$ is the fractional concentration of exchangeable hydroxyl protons of the glycogen with respect to the water protons, $t_{sat}$ is the saturation time (that is, the length of time of irradiation of the glycogen or glucose hydroxyl protons), $\alpha$ is the saturation efficiency, and the term $k_{exch} \cdot x_{glyc}$ accounts for exchange of saturated protons from water molecules back to the glycogen or glucose. Such back-exchange can be substantial when the exchange rate $k_{exch}$ and/or the concentration of exchangeable protons for glycogen $x_{glyc}$ is high. The expression of Equation (2) can be related to the proton transfer enhancement (PTE) for glycogen or glucose, which depends on the number of protons per molecular weight unit ($N_{glyc}$) and the molecular weight ($M_{glyc}$) of the glycogen or glucose, as follows:

$$PTE = \frac{N_{glyc} \cdot M_{glyc}}{x_{glyc}} \cdot PTR. \qquad (3)$$

Some typical in vivo parameter values expected for a human subject are: exchange rate $k_{exch}$=5000 Hz; $R_{1w}$32 1 second, saturation efficiency $\alpha$=0.5; and $t_{sat}$=1 second. For a human liver (~200 mM glycogen in glucose unit concentration), muscle ($\simeq$80 mM), and brain ($\simeq$3 mM), PTR effects of 49%, 47%, and 14% are estimated for these parameters.

This estimation may not be precise as exchange is rapid and the glycogen resonances are close to water. A more accurate estimate can be obtained by solving all six Bloch Equations. However, the order of magnitude given by Equation (2) should be reasonable. Equation (2) shows that the PTR should exhibit substantial sensitivity to glycogen content, pH (which influences the exchange rate $k_{exch}$) and water content (which influences $R_{1w}$). Interestingly, Equation (2) predicts that PTR will reduce strongly during glycogen depletion and will also reduce during pH reduction, such as during ischemia. Thus, it is anticipated that the glycogen spatially resolved detection, imaging, or mapping techniques disclosed herein will enable measurement of ischemic effects and exercise-related variations in glycogen levels with high sensitivity. As another contemplated application, since tumors typically have limited amounts of glycogen, it should be possible to detect tumors using this approach in tissues with a high glycogen concentration, for example liver and muscle.

Figure 3:
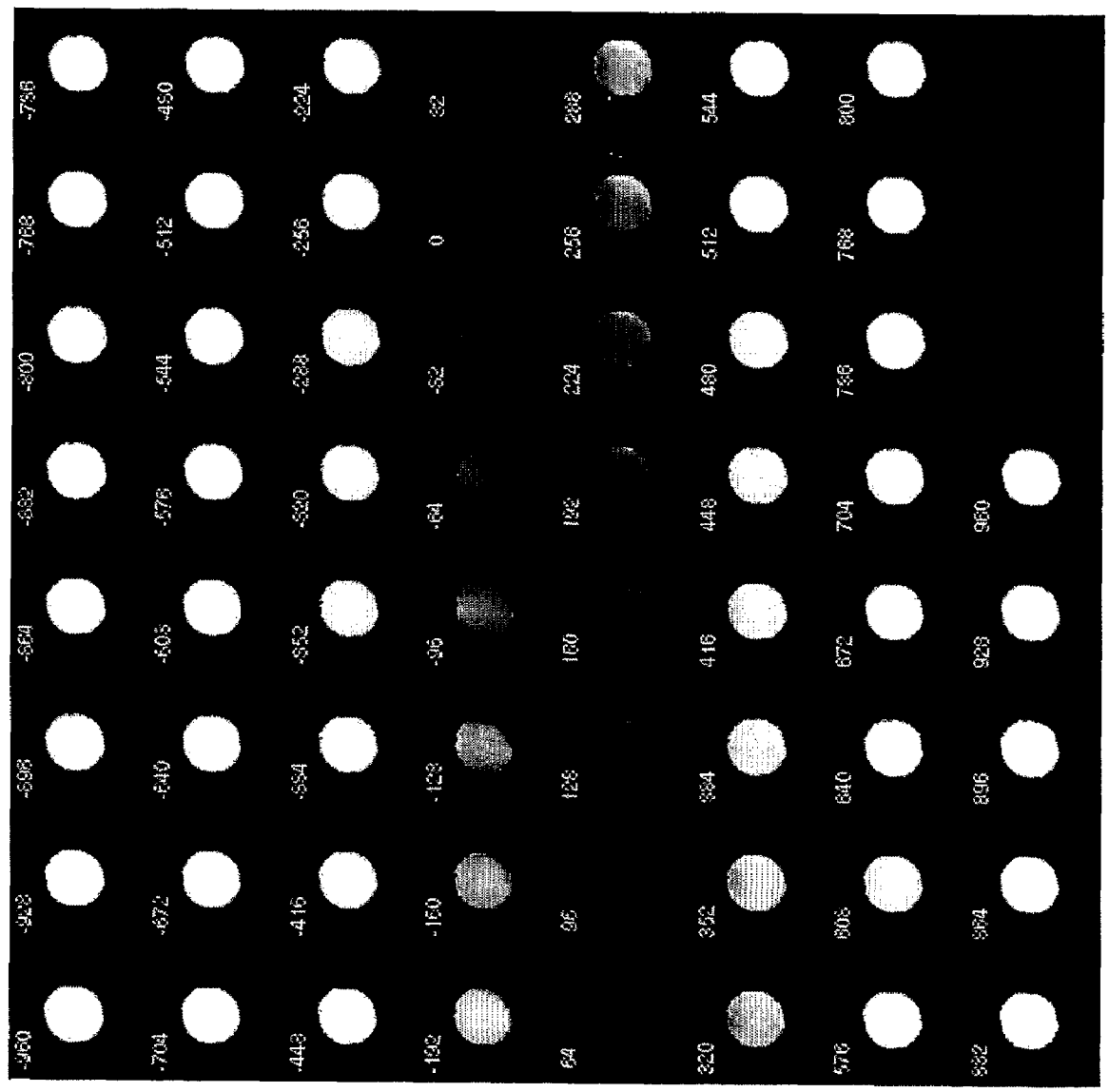
Figure 4:
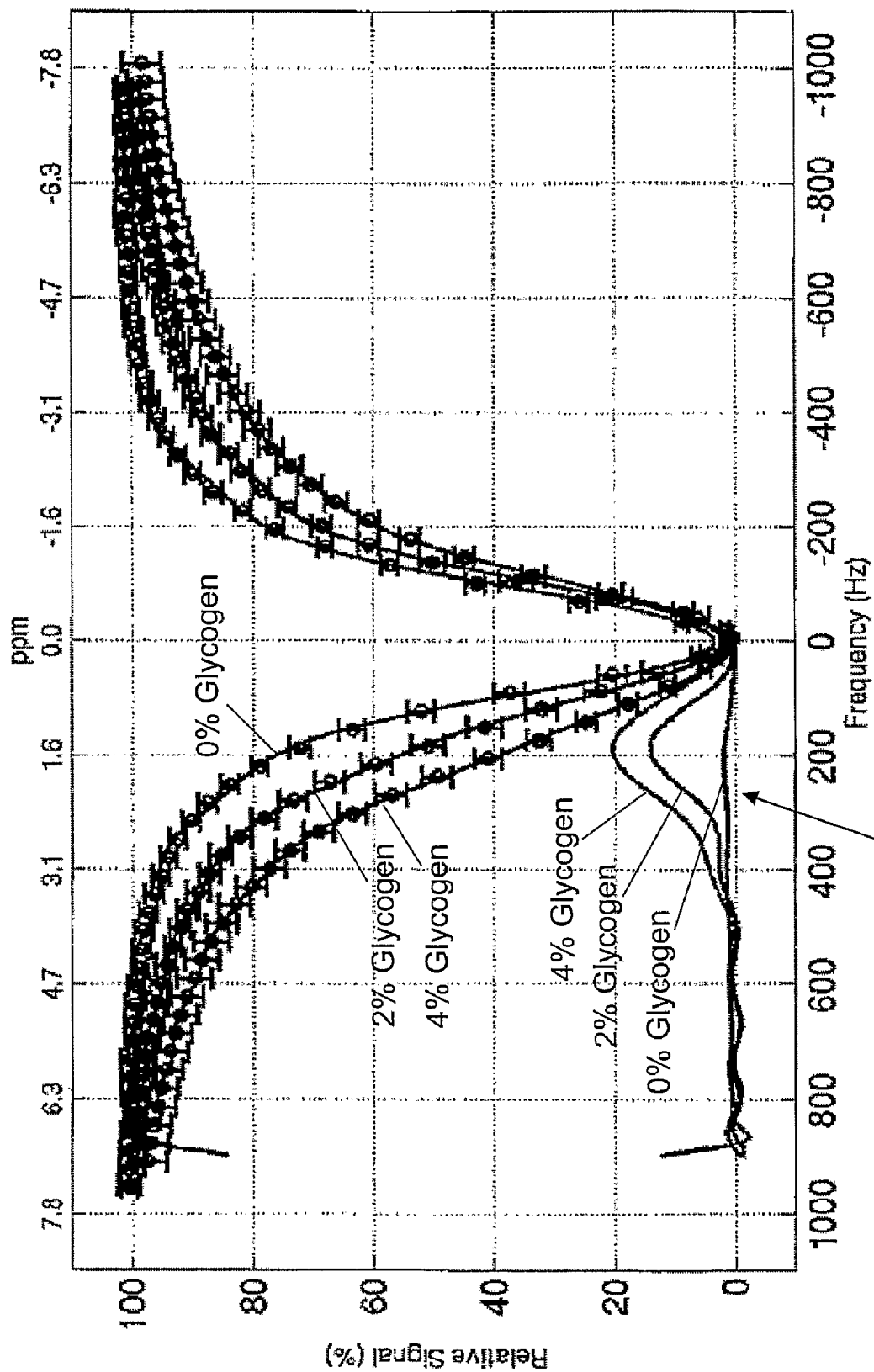

With reference to FIGS. 3 and 4, a set of phantoms of different glycogen concentrations was fabricated as follows. Three solutions of concentration 0%, 2% and 4% (w/vol) of glycogen (bovine liver, Type 1X G0885 from Sigma CAS# 9005-79-2, molecular weight (MW) estimated~50 kD), along with sodium azide were mixed in flask on a hot plate. Once the glycogen was mixed, the pH was adjusted to about 7.1 and solutions were sealed in 500 ml containers. With brief reference back to FIG. 1, the phantoms were placed in the radio frequency coil 30 which was a bird-cage transmit/receive radio frequency coil and scanned using a magnetic resonance scanner 10 which was a 3T Philips Intera scanner (available from Koninklijke Philips Electronics N. V., Eindhoven, The Netherlands). The glycogen phantoms were each scanned using the glycogen sequence 44 including a saturation pulse of power level 3 µT (duration 3 seconds) and a turbo spin-echo image acquisition (TSE factor=34). More generally, the glycogen sequence 44 can employ substantially any type of image acquisition sequence. Other imaging parameters used were: single slice 5 mm thick, TR=5 seconds, time-to-echo (TE)=11.5 milliseconds, field-of-view (FOV)=160 centimeters, 128×128 acquisition. Data in the form of z-spectra were acquired using sixty-one different irradiation frequencies ($\omega$=0, 32, −32, 64, −64, . . . , 960, −960 Hz) for the saturation pulse, and a reference image $S_0$ with no saturation pulse. A region of interest was drawn in the reference image $S_0$. The mean and standard deviation of the normalized signal intensity ($S(\omega)/S_0$*100) was calculated. FIG. 3 shows images of the phantoms as a function of the radio frequency off-resonance in Hertz (shown above and to the left of each phantom). FIG. 4 shows the relative signal intensity of the regions of interest for the 0%, 2%, and 4% glycogen phantoms as a function of the 63 frequency offsets of the saturation pulse. Curves 100 in the lower left side of the plot of FIG. 4 are the asymmetry differences $S_{asym}(\omega)$ of the 0%, 2%, and 4% phantoms calculated by subtracting the left (high frequency) side of the data from the right (low frequency) side of the data in accordance with Equation (1). The normalized area under the curve of the asymmetry differences are 0, 2.12, and 3.99 for the 0%, 2% and 4% glycogen phantoms, respectively.

In another actually performed process, the liver of a healthy volunteer was scanned three times using z-spectroscopy combined with imaging. The first scan was after a fast of approximately 18 hours from the previous meal. Food was then consumed (five slices of 7-grain bread with apricot jelly plus two cookies). Ten minutes after the food was consumed a second glycogen scan was acquired at the same anatomical location. A third glycogen scan was acquired 30 minutes after eating. The healthy, normal volunteer was scanned on a 3T Philips magnetic resonance scanner using body coil excitation and SENSE detection. A six element parallel imaging cardiac-type receive coil was placed around the thoracic part of the abdomen. The body coil was used for radio frequency transmission. An axial image though the spine between thoracic vertebrae T8 and T9 was chosen as the glycogen imaging slice. An image from the same anatomical slice was acquired 35 times with the frequency offset $\omega$ of the radio frequency saturation pulse changed for each acquisition: $\omega$=0, 64, −64, 128, −128, . . . , 1024, −1024 Hz offset from the water frequency. The RF saturation pulse had a duration of 500 milliseconds and an amplitude of 3 µT. Other imaging parameters included: TR/TE=5000/80 milliseconds, FOV=375 millimeters, TSE factor=30, and SENSE factor=2. Second order shims were optimized over the liver so as to minimize the $B_0$ field inhomogeneity. Data acquisition was triggered to the respiration so as to minimize artifacts due to respiratory motion. The volunteer was scanned three times using this sequence: once before eating (but after the 18 hour fast); ten minutes after eating; and thirty minutes after eating.

A z-spectrum was calculated from each of the three scans and was defined to be the relative signal intensity plotted as a function of frequency offset. The relative signal intensity was defined as $S(\omega)/S_0$ where $S(\omega)$ is the mean signal intensity over the region of interest in the image acquired with a saturation pulse at frequency $\omega$ and $S_0$ is the mean signal intensity in the region of interest in the reference image (that is, the image acquired with no radio frequency saturation). The asymmetry $S_{asym}(\omega)$ of the z-spectrum was calculated using Equation (1).

Figure 5:
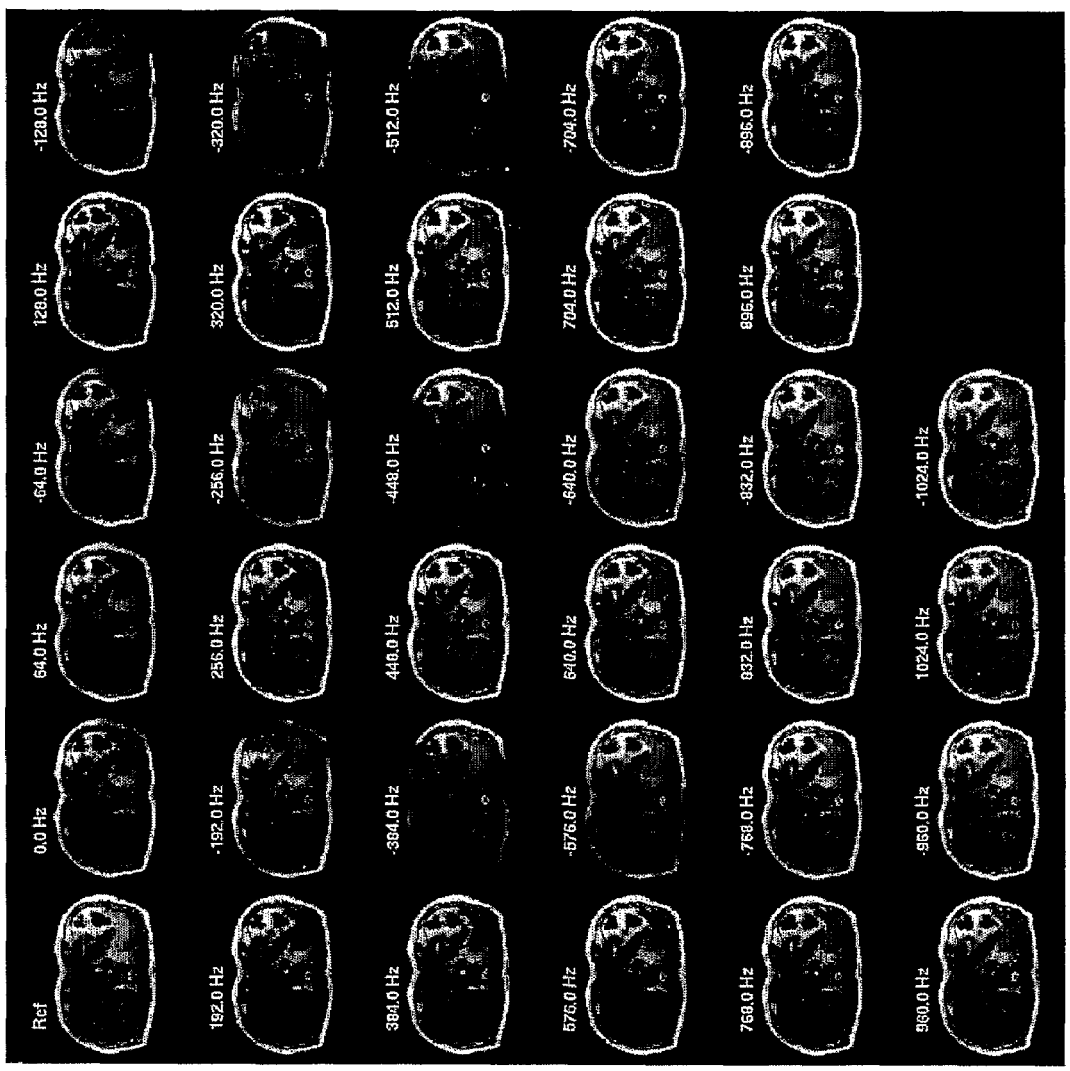

With reference to FIG. 5, axial image slices acquired between thoracic vertebrae T8 and T9 of the human volunteer subject after saturation at frequency $\omega$ are shown. The saturation frequency co respective to the water line (0.0 Hz) is labeled at the upper left of each image. Asymmetry respective to the water line is clearly seen by comparing the images acquired after saturation at positive and negative saturation frequencies respective to the 0.0 Hz (0.0 ppm) water line.

Figure 6:
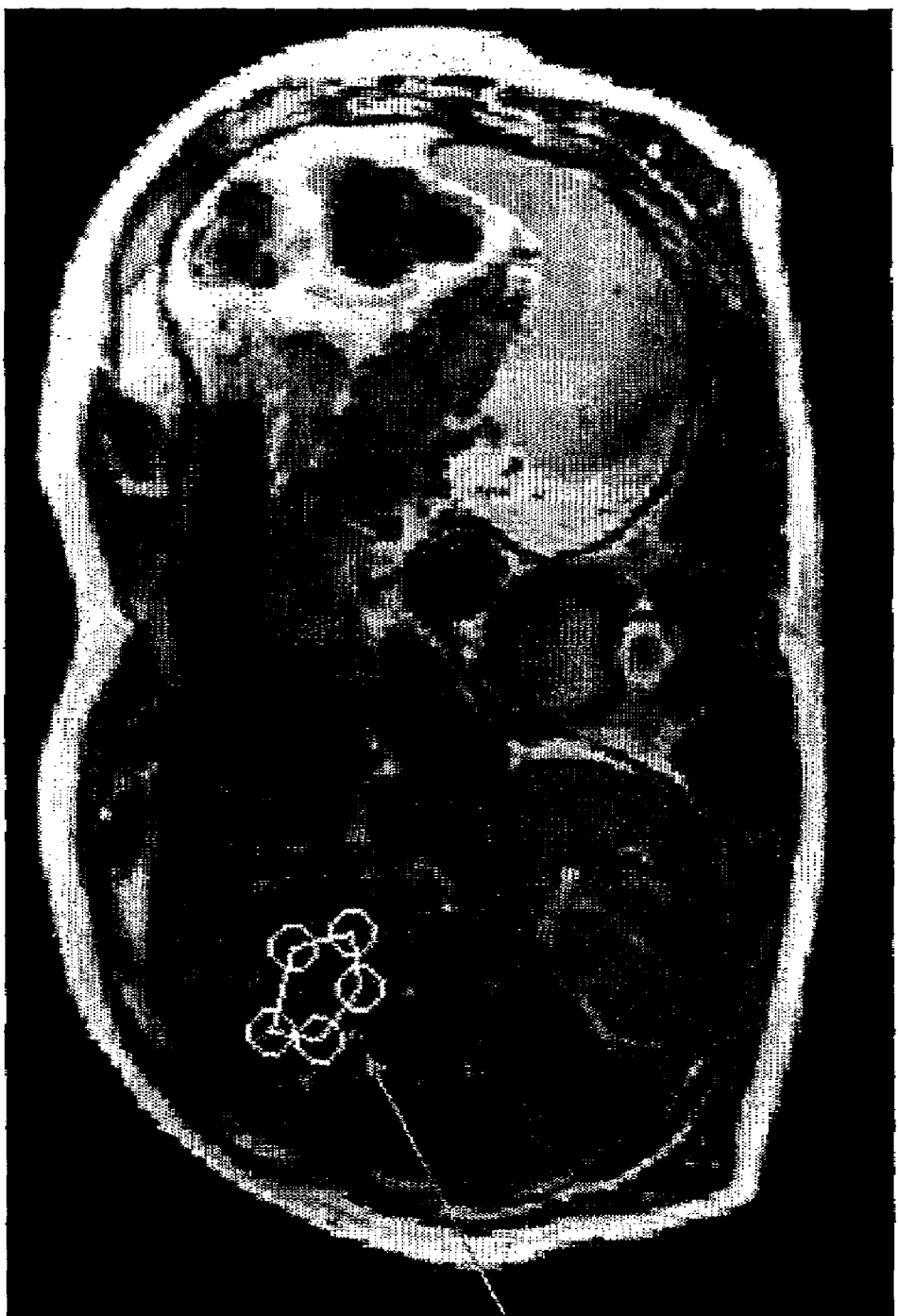

With reference to FIG. 6, an axial reference image acquired between thoracic vertebrae T8 and T9 of the human volunteer subject is shown. This reference image was acquired without radio frequency saturation. The left side of the image is the right side of the volunteer. The mean and standard deviation of the signal intensity was calculated over the voxels in a region of interest 102. This mean and standard deviation was also calculated in the image for each saturation frequency offset and for each condition (i.e., before eating, ten minutes after eating, and thirty minutes after eating).

Figure 7:
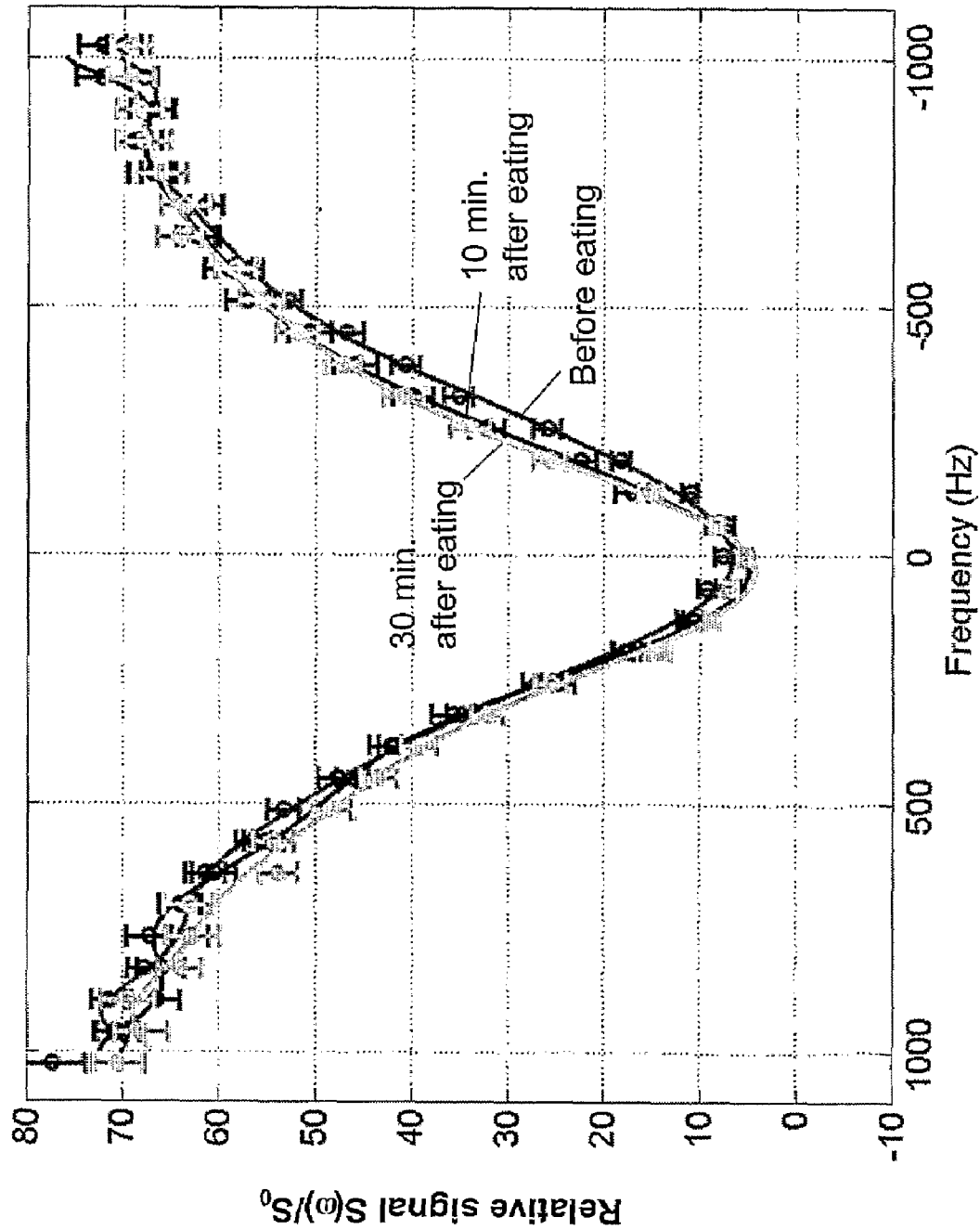
FIG. 7 shows the z-spectra for the mean of the signal intensity over the volume elements that compose the region of interest indicated in FIG. 6, for the data acquired under three conditions of before eating after about 18 hours of fasting to reduce liver glycogen, ten minutes after eating, and thirty minutes after eating.

With reference to FIG. 7, the z-spectra for the mean of the signal intensities of the region of interest 102 are shown for the data acquired under the three conditions of before eating, ten minutes after eating, and thirty minutes after eating. The magnetization transfer effect is seen to be quite similar for all three situations, but the shape of the curves is somewhat different.

Figure 8:
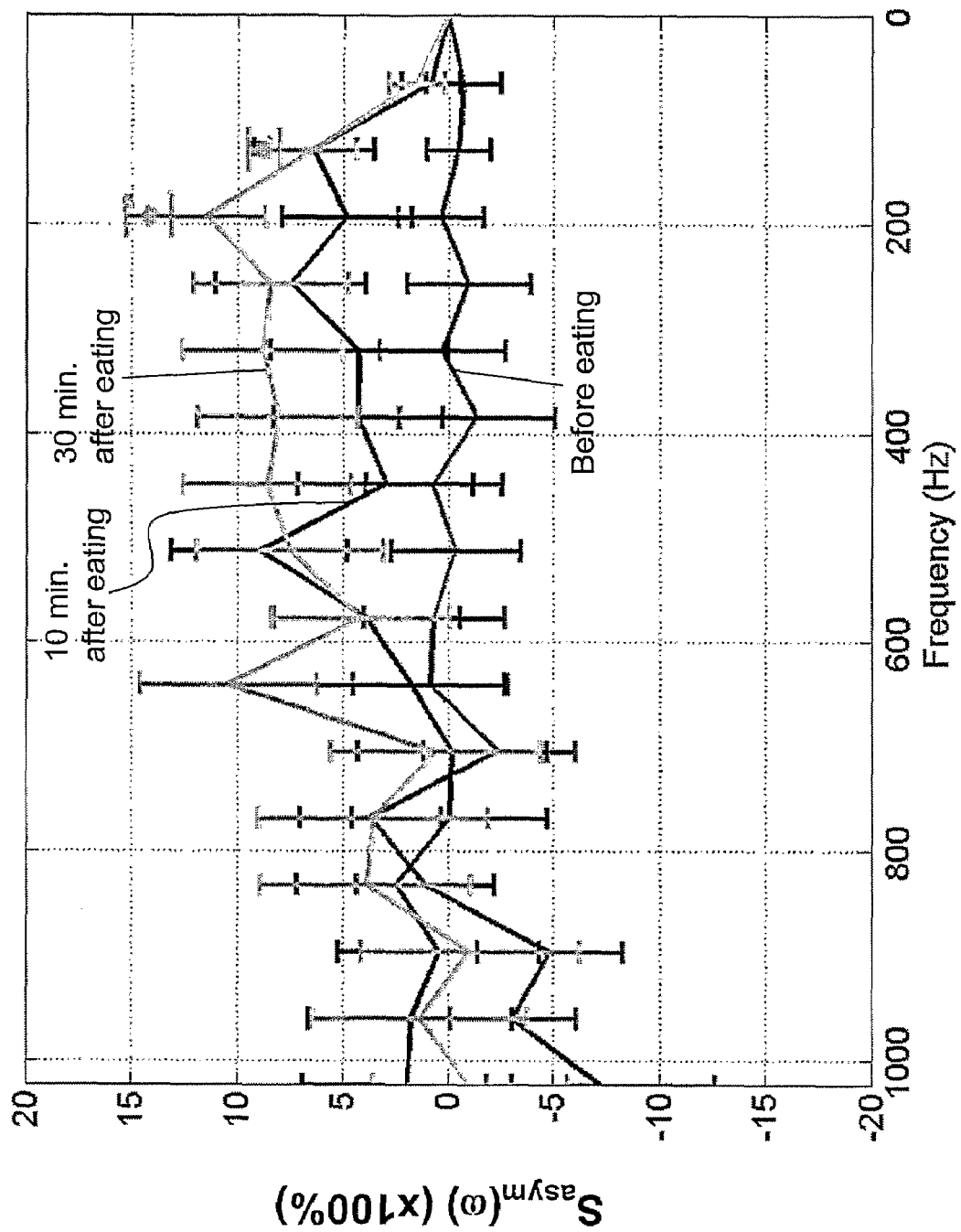
FIG. 8 shows a plot of asymmetry $S_{asym}(\omega)$ of the z-spectrum for the region of interest indicated in FIG. 6, plotted as percentage values versus saturation frequency for the three conditions of before eating after 18 hours of fasting, ten minutes after eating, and thirty minutes after eating.

With reference to FIG. 8, the asymmetry plot of $S(\omega)$ of Equation (1) plotted as percentage values versus saturation frequency is shown for the three conditions of before eating, ten minutes after eating, and thirty minutes after eating. The asymmetry is near 0% for the data acquired before eating. The asymmetry is near 5% for the data acquired ten minutes after eating, and is near 9% for the data acquired thirty minutes after eating. This increasing asymmetry corresponds to an expected increase in the glycogen concentration will typically occurs shortly after eating if the person has fasted considerably before the eating.

With reference to FIG. 9, the integral under the asymmetry curve was calculated for each voxel in the image for the condition of before eating (left side image of FIG. 9) and for the condition of thirty minutes after eating (right hand image of FIG. 9). Comparison of these images or maps shows increased liver glycogen content after eating, since the signal intensity is greater in the image or map for the condition of thirty minutes after eating compared with the image or map for the condition of before eating. In the images or maps of FIG. 9, the fat signal is negative, which indicates a large proton transfer effect for fat protons. The stomach also shows high asymmetry, which is believed to be attributable to glucose-related compounds for which OH exchange is observable at low pH.

In summary, the phantom data of FIGS. 2-4 show that the saturation transfer effect from exchangeable protons in endogenous glycogen to tissue water protons is a sensitive measure to quantify the endogenous glycogen content using a magnetic resonance scanner. The relative measures of glycogen calculated from the image intensities are very similar to the known concentration changes. Absolute in vivo endogenous glycogen or glucose concentrations can be calibrated using calibration based on known glycogen concentrations in certain tissues, or by changing glycogen concentrations in tissue or using $^{13}C$ spectroscopy in tissue. The latter would have to be done over larger regions of interest due to the limited sensitivity of 13C MR. The in vivo data of FIGS. 5-9 acquired from a liver of a human volunteer subject show that a simple fasting/feeding regimen can be detected using the disclosed glycogen spatially resolved detection, imaging, or mapping approaches disclosed herein.

In the described embodiments, the magnetization at the magnetic resonance frequency of protons of hydroxyl groups of endogenous glucose or glycogen is partially or fully saturated, and water proton magnetic resonance data are acquired while the saturation is in effect. More generally, a selected noninvasive modification or noninvasive magnetic labeling is made of magnetic resonance at the magnetic resonance frequency of protons of hydroxyl groups of endogenous glucose or glycogen, probative water proton magnetic resonance data are acquired while the magnetic labeling is substantially in effect, and information about glucose or glycogen concentration or density is derived based at least on the probative water proton magnetic resonance data. It is contemplated to substitute another magnetic labeling for the described saturation of magnetic resonance at the magnetic resonance frequency of protons of hydroxyl groups of glucose or glycogen. For example, the selected magnetic labeling at the magnetic resonance frequency of protons of hydroxyl groups of glucose or glycogen may be an inversion recovery pulse, a dephasing pulse, or any type of frequency-specific magnetic resonance-based labeling, or so forth. Further, it is contemplated to apply the approaches disclosed herein for spatially resolved detection, imaging, or mapping of selected endogenous monosaccharides or polysaccharides other than glucose or glycogen, by substituting the magnetic resonance frequency of protons of hydroxyl groups of the selected monosaccharide or polysaccharide for the magnetic resonance frequency of protons of hydroxyl groups of glucose or glycogen.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A magnetic resonance method comprising:
    making a selected modification at a magnetic resonance frequency of exchangeable protons of hydroxyl groups of a selected monosaccharide or polysaccharide, the selected modification being an in vivo modification comprising saturation of magnetic resonance or non-invasive magnetic labeling;
    acquiring probative water proton magnetic resonance data in vivo while the in vivo saturation or non-invasive magnetic labeling is substantially in effect; and
    deriving information about in vivo concentration or density of the selected monosaccharide or polysaccharide based at least on the probative water proton magnetic resonance data.

2. The magnetic resonance method as set forth in claim 1, further including:
    acquiring reference water proton magnetic resonance data in vivo that is substantially not influenced by exchange of water protons with in vivo saturated or non-invasively magnetically labeled protons of hydroxyl groups of the selected monosaccharide or polysaccharide, the deriving includes comparing or combining the probative water proton magnetic resonance data and the reference water proton magnetic resonance data.

3. The magnetic resonance method as set forth in claim 1, wherein the selected monosaccharide or polysaccharide is glucose or glycogen.

4. The magnetic resonance method as set forth in claim 3, further including:
    acquiring reference water proton magnetic resonance data in vivo that is substantially not influenced by exchange of water protons with in vivo saturated or non-invasively magnetically labeled protons of glucose or glycogen, the deriving including comparing or combining the probative water proton magnetic resonance data acquired in vivo and the reference water proton magnetic resonance data acquired in vivo.

5. The magnetic resonance method as set forth in claim 4, further including:
    reconstructing the probative water magnetic resonance data acquired in vivo to form a probative water image; and
    reconstructing the reference water magnetic resonance data acquired in vivo to form a reference water image, the deriving including comparing or combining the probative water image and the reference water image to generate a glucose or glycogen image or map.

6. The magnetic resonance method as set forth in claim 3, wherein:
the in vivo saturating or non-invasive magnetic labeling includes saturating or non-invasively magnetically labeling at each of a plurality of different frequencies, the plurality of different frequencies being substantially centered around the water proton magnetic resonance frequency and encompassing the magnetic resonance frequency of protons of hydroxyl groups of glucose or glycogen;
the acquiring includes acquiring probative water proton magnetic resonance data after the in vivo saturating or non-invasively magnetically labeling at each frequency; and
the deriving includes generating a z-spectrum from the probative water proton magnetic resonance data.

7. The magnetic resonance method as set forth in claim 3, wherein:
the acquiring of probative water proton magnetic resonance data in vivo includes acquiring probative water proton magnetic resonance imaging data; and
the deriving includes deriving a glucose or glycogen image or map indicative of spatial distribution of glucose or glycogen from the probative water proton magnetic resonance imaging data.

8. The magnetic resonance method as set forth in claim 1, wherein the deriving includes:
measuring the influence of pH on the probative water proton magnetic resonance data acquired in vivo.

9. The magnetic resonance method as set forth in claim 8, wherein the deriving further includes:
computing the information about the in vivo concentration or density of the selected monosaccharide or polysaccharide at least in part based on a forward rate of exchange ($k_{exch}$) of exchangeable protons of hydroxyl groups of the selected monosaccharide or polysaccharide with protons of water, said forward rate of exchange ($k_{exch}$) being influenced by the pH.

10. The magnetic resonance method as set forth in claim 1, wherein the making of the selected modification includes:
saturating magnetic resonance in vivo at each of a plurality of frequencies, the plurality of frequencies encompassing the magnetic resonance frequency of the protons of hydroxyl groups of the selected monosaccharide or polysaccharide, the acquiring including acquiring probative magnetic resonance data in vivo after each saturation operation.

11. The magnetic resonance method as set forth in claim 10, further including:
acquiring reference magnetic resonance data in vivo around the magnetic resonance frequency of water protons, the acquired reference magnetic resonance data being substantially not influenced by the in vivo saturation, the deriving including comparing or combining the probative and reference magnetic resonance data.

12. The magnetic resonance method as set forth in claim 10, wherein the deriving includes:
computing an asymmetry based on $S(-\omega)$ and $S(+\omega)$, where $S(+\omega)$ denotes the water signal after saturating in vivo at $+\omega$, $-\omega$ denotes the magnetic resonance frequency symmetrically positioned on the opposite side of the water proton magnetic resonance frequency from $+\omega$, and $S(-\omega)$ denotes the water signal after saturating in vivo at $-\omega$.

13. The magnetic resonance method as set forth in claim 12, wherein the deriving of information about in vivo concentration or density of the selected monosaccharide or polysaccharide further includes:
calculating an image or map of the selected monosaccharide or polysaccharide based on the computed asymmetry.

14. The magnetic resonance method as set forth in claim 12, wherein the computing of the asymmetry is further based on $S_0$, where $S_0$ is a reference signal acquired without saturation.

15. The magnetic resonance method as set forth in claim 10, wherein the selected monosaccharide or polysaccharide is glucose or glycogen, and the acquiring of probative water proton magnetic resonance data in vivo while the in vivo saturation or non-invasive magnetic labeling is substantially in effect includes:
acquiring probative magnetic resonance imaging data, the information about the in vivo concentration or density of the selected monosaccharide or polysaccharide including an image or map of glucose or glycogen density or concentration derived from the probative magnetic resonance imaging data.

16. The magnetic resonance method as set forth in claim 10, wherein the plurality of frequencies are substantially centered with respect to the magnetic resonance frequency of water protons, and the deriving includes:
constructing a z-spectrum from the probative magnetic resonance data acquired in vivo; and
performing further processing based on the z-spectrum, the further processing including at least one of:
calculating an image or map of the selected monosaccharide or polysaccharide based on z-spectra constructed for different voxels, and
estimating the in vivo concentration or density of the selected monosaccharide or polysaccharide based on an asymmetry of the constructed z-spectrum.

17. The magnetic resonance method as set forth in claim 4, wherein the probative and reference water proton magnetic resonance data are spatially encoded imaging data, and the deriving includes:
reconstructing a probative water proton magnetic resonance image from the probative water proton magnetic resonance imaging data acquired in vivo;
reconstructing a reference water proton magnetic resonance image from the reference water proton magnetic resonance imaging data acquired in vivo; and
deriving an image or map of the selected monosaccharide or polysaccharide concentration or density based on the probative and reference water proton magnetic resonance images.

18. The magnetic resonance method as set forth in claim 1, wherein the selected monosaccharide or polysaccharide is glucose or glycogen and the making of the selected in vivo modification comprising saturation of magnetic resonance or non-invasive magnetic labeling includes making a modification selected from the group consisting of (i) saturating magnetic resonance at the magnetic resonance frequency of protons of hydroxyl groups of glucose or glycogen, (ii) applying an inversion recovery pulse at the magnetic resonance frequency of protons of hydroxyl groups of glucose or glycogen, (iii) applying a dephasing pulse at the magnetic resonance frequency of protons of hydroxyl groups of glucose or glycogen, (iv) performing magnetic labeling of the hydroxyl protons of glucose or glycogen, and (v) any other radio frequency-based or magnetic resonance-based labeling.

19. The magnetic resonance method as set forth in claim 1, wherein the magnetic resonance method does not include administering an exogenous contrast agent to the subject.

20. The magnetic resonance method as set forth in claim 19, wherein the subject is an in vivo human subject.

21. A magnetic resonance apparatus comprising:
means for making a selected modification at a magnetic resonance frequency of exchangeable protons of hydroxyl groups of a selected endogenous monosaccharide or polysaccharide, the selected modification being an in vivo modification comprising saturation of hydroxyl protons or non-invasive magnetic labeling of hydroxyl protons of the selected endogenous monosaccharide or polysaccharide in an in vivo subject;
means for acquiring probative water proton magnetic resonance data in vivo while the in vivo saturation or non-invasive magnetic labeling is substantially in effect; and
means for deriving information about in vivo concentration or density of the selected endogenous monosaccharide or polysaccharide based at least on the probative water proton magnetic resonance data.

22. The magnetic resonance apparatus as set forth in claim 21, further including:
means for acquiring reference water proton magnetic resonance data in vivo that is substantially not influenced by exchange of water protons with in vivo saturated or non-invasively magnetically labeled hydroxyl protons of the selected endogenous monosaccharide or polysaccharide, the deriving includes comparing or combining the probative water proton magnetic resonance data and the reference water proton magnetic resonance data.

23. The magnetic resonance apparatus as set forth in claim 21, wherein the selected endogenous monosaccharide or polysaccharide is glucose or glycogen, and the magnetic resonance apparatus does not include a means for administering an exogenous contrast agent to the subject.

24. The magnetic resonance apparatus as set forth in claim 21, wherein the selected modification means includes:
means for saturating magnetic resonance in vivo at each of a plurality of frequencies, the plurality of frequencies encompassing the magnetic resonance frequency of the protons of hydroxyl groups of the selected endogenous monosaccharide or polysaccharide, the acquiring including acquiring probative magnetic resonance data in vivo after each saturation operation.

* * * * *